(12) United States Patent
Mukaide

(10) Patent No.: US 9,234,856 B2
(45) Date of Patent: Jan. 12, 2016

(54) X-RAY APPARATUS AND X-RAY MEASURING METHOD

(75) Inventor: Taihei Mukaide, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 323 days.

(21) Appl. No.: 13/809,335

(22) PCT Filed: Aug. 1, 2011

(86) PCT No.: PCT/JP2011/068000
§ 371 (c)(1),
(2), (4) Date: Jan. 9, 2013

(87) PCT Pub. No.: WO2012/018129
PCT Pub. Date: Feb. 9, 2012

(65) Prior Publication Data
US 2013/0108020 A1    May 2, 2013

(30) Foreign Application Priority Data
Aug. 6, 2010    (JP) .................................. 2010-177062

(51) Int. Cl.
*G01N 23/04*    (2006.01)
*G01N 23/20*    (2006.01)
(Continued)

(52) U.S. Cl.
CPC ................ *G01N 23/20* (2013.01); *G01N 23/04* (2013.01); *G01N 23/083* (2013.01); *G21K 1/06* (2013.01); *G21K 2201/06* (2013.01); *G21K 2201/067* (2013.01); *G21K 2207/005* (2013.01)

(58) Field of Classification Search
USPC ........................................................ 378/62
See application file for complete search history.

(56) References Cited

U.S. PATENT DOCUMENTS

| 8,036,336 B2 | 10/2011 | Mukaide et al. |
| 8,509,382 B2 | 8/2013 | Mukaide et al. |

(Continued)

FOREIGN PATENT DOCUMENTS

| CN | 101011254 | 8/2007 |
| CN | 101257851 | 9/2008 |

(Continued)

OTHER PUBLICATIONS

Office Action issued on Mar. 18, 2014 in counterpart Jap[anise patent application 2011-177062, with partial translation.

(Continued)

*Primary Examiner* — Phillip A Johnston
*Assistant Examiner* — Hsien Tsai
(74) *Attorney, Agent, or Firm* — Fitzpatrick, Cella, Harper & Scinto

(57) ABSTRACT

An apparatus for deriving X-ray absorbing and phase information comprises; a splitting element for splitting spatially an X-ray, a detector for detecting intensities of the X-rays transmitted through an object, the intensity of the X-rays changing according to X-ray phase and also position changes, and an calculating unit for calculating an X-ray transmittance image, and an X-ray differential phase contrast or phase sift contrast image as the phase information. The X-ray is split into two or more X-rays having different widths, and emitted onto the detector unit. And, the calculating unit calculates the X-ray absorbing and phase information based on a difference, between the two or more X-rays, in correlation between the changing of the phase of the X-ray and the changing the intensity of the X-ray in the detector unit.

12 Claims, 10 Drawing Sheets

(51) Int. Cl.
    *G01N 23/083*   (2006.01)
    *G21K 1/06*    (2006.01)

(56) References Cited

U.S. PATENT DOCUMENTS

| | | | |
|---|---|---|---|
| 8,588,366 B2* | 11/2013 | Mukaide et al. | 378/62 |
| 8,638,903 B2* | 1/2014 | Mukaide et al. | 378/36 |
| 2007/0183581 A1 | 8/2007 | Heismann et al. | 378/145 |
| 2007/0183584 A1 | 8/2007 | Baumann et al. | 378/145 |
| 2009/0092227 A1 | 4/2009 | David et al. | 378/36 |
| 2010/0220834 A1 | 9/2010 | Heismann et al. | 378/19 |
| 2010/0260315 A1* | 10/2010 | Sato | G21K 1/06 378/36 |
| 2011/0064196 A1* | 3/2011 | Mukaide | G21K 1/06 378/62 |
| 2011/0158389 A1 | 6/2011 | Mukaide et al. | 378/62 |
| 2011/0176662 A1 | 7/2011 | Watanabe et al. | 178/62 |
| 2011/0194674 A1 | 8/2011 | Mukaide et al. | |
| 2011/0206184 A1 | 8/2011 | Mukaide et al. | 178/62 |
| 2013/0142307 A1* | 6/2013 | Nakamura | A61B 6/484 378/62 |

FOREIGN PATENT DOCUMENTS

| | | |
|---|---|---|
| EP | 1879020 | 1/2008 |
| GB | 2441578 | 3/2008 |
| JP | 2001-212127 | 8/2001 |
| JP | 2002-102215 | 4/2002 |
| JP | 2007-203063 | 8/2007 |
| JP | 2011-011039 | 1/2011 |
| JP | 2011-022134 | 2/2011 |
| JP | 2011-041795 | 3/2011 |
| WO | WO 2008/029107 | 3/2008 |
| WO | WO 2010/047401 | 4/2010 |
| WO | WO 2010/082688 | 7/2010 |

OTHER PUBLICATIONS

Office Action issued on Jul. 1, 2014, in counterpart Chinese (P.R.C.) patent application 201180037916.9, with translation.

* cited by examiner

X-RAY APPARATUS AND X-RAY MEASURING METHOD

TECHNICAL FIELD

The present invention relates to an X-ray imaging apparatus and an X-ray imaging method.

BACKGROUND ART

A nondestructive testing method using radiation has been used in a wide range of fields from industrial applications to medical applications.

For example, the X-ray refers to an electromagnetic wave with a wavelength of about 1 pm to 10 nm ($10^{-12}$ to $10^{-8}$ m). Of them, the X-ray with a short wavelength (about 2 keV or more) is referred to as a hard X-ray, and the X-ray with a long wavelength (about 0.1 keV to about 2 keV) is referred to as a soft X-ray.

For example, there is known an absorption contrast method of obtaining an absorption image using a difference in transmittance when an X-ray is transmitted through an object. The method using a high X-ray transmittance has been practically used for an internal crack inspection of an iron and steel material and an application in a security field such as a baggage inspection.

Meanwhile, when the object is made of substances with a density difference too small to detect a change in contrast by X-ray absorption, X-ray phase contrast imaging is effective in detecting an X-ray phase shift through the object. For example, the X-ray phase contrast imaging is expected to be applied to imaging of a polymer blend and a medical application.

Of the various X-ray phase contrast imaging methods, the method disclosed in PTL 1 is very simple and effective in using a refraction effect to detect a phase shift through the X-rayed object. Specifically, the method is such that an X-ray source with a micro focus is used; the object and the detector are spaced away from each other; and thereby, the object is detected with its edge enhanced due to the refraction effect through the X-rayed object.

In addition, unlike many X-ray phase contrast imaging methods, the method of using the refraction effect is characterized in that a high coherence X-ray beam such as a synchrotron radiation beam is not always required.

Meanwhile, PTL 2 discloses an imaging apparatus installing an X-ray shielding mask in an edge portion of a pixel of the detector.

In the absence of the object, when setting is performed in such a manner that an X-ray is emitted to part of the shielding mask, an X-ray positional change due to the object refraction effect can be detected as an intensity change.

CITATION LIST

Patent Literature

PTL 1: Japanese Patent Application Laid-Open No. 2002-102215
PTL 2: International Patent Publication No. WO2008/029107

SUMMARY OF INVENTION

Technical Problem

Unfortunately, in the conventional methods such as PTL 1 and PTL 2, absorption information (X-ray transmittance image) and phase information (X-ray differential phase contrast image and X-ray phase shift image) about the X-rayed object are not discriminated from each other.

Thus, the conventional methods have a problem in that the absorption information and the phase information cannot be obtained in a separate and independent manner.

In view of this, it is an object of the present invention to provide an X-ray apparatus and an X-ray measuring method capable of obtaining absorption information (X-ray transmittance image) and phase information (X-ray differential phase contrast image and X-ray phase shift image) about an X-rayed object as separate and independent information.

Solution to Problem

The present invention provides an X-ray apparatus and an X-ray measuring method having the following configuration.

According to an aspect of the present invention, an X-ray apparatus for deriving X-ray absorbing information and X-ray phase information of an object to be detected comprises: a splitting element for splitting spatially an X-ray generated by an X-ray generating unit; a detector unit for detecting intensities of the X-rays, based on the X-rays split by the splitting element and transmitted through the object, the intensity of the X-rays changing according to an X-ray phase shift during the transmitting through the object, and also changing according to an X-ray position change; and an calculating unit for calculating an X-ray transmittance image as the X-ray absorbing information, and an X-ray differential phase contrast image or an X-ray phase sift image as the X-ray phase information, wherein the splitting element splits the X-ray into two or more the X-rays having different widths, and emitting the X-rays onto the detector unit, and the calculating unit calculates the X-ray absorbing information and the X-ray phase information based on a difference, between the two or more X-rays, in correlation between the changing of the phase of the X-ray and the changing the intensity of the X-ray in the detector unit.

According to a further aspect of the present invention, an X-ray measuring method for deriving X-ray absorbing information and X-ray phase information of an object to be detected comprises steps of: splitting spatially an X-ray generated by an X-ray generator into two or more X-rays having different widths; detecting intensities of the X-rays, based on the X-rays split by the splitting step and transmitted through the object, the intensity of the X-ray changing according to an X-ray phase shift during the transmitting through the object, and also changing according to an X-ray position change; and calculating an X-ray transmittance and the X-ray position change of the object, based on a difference, between the two or more X-rays, in a correlation between the changing of the phase of the X-ray and the changing of the X-ray intensity in the detector unit.

Advantageous Effects of Invention

The present invention can provide an X-ray apparatus and an X-ray measuring method capable of obtaining absorption information (X-ray transmittance image) and phase information (X-ray differential phase contrast image and X-ray phase shift image) about an object as separate and independent information.

Further features of the present invention will become apparent from the following description of exemplary embodiments with reference to the attached drawings.

DESCRIPTION OF EMBODIMENTS

Figure 1:
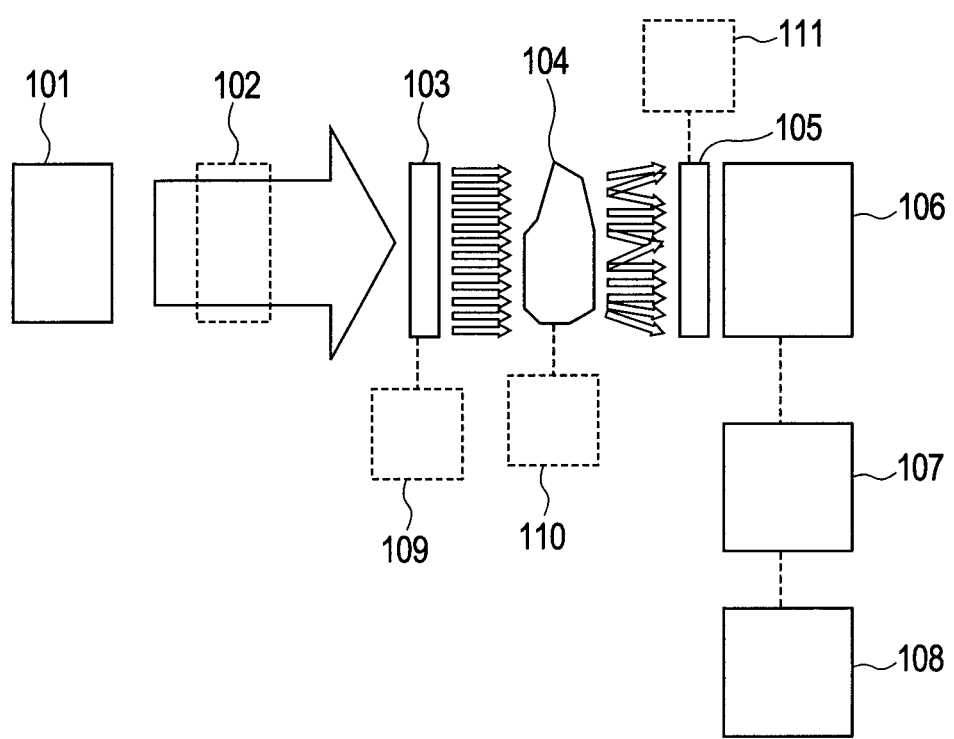
FIG. 1 is a drawing illustrating a configuration example of an X-ray apparatus according to first, second, and third embodiments.

Embodiments of the present invention relate to an X-ray apparatus using a phase shift through an object, and the X-ray apparatus and the X-ray measuring method capable of obtaining absorption information and phase information about the X-rayed object as separate and independent information will be described.

The X-ray apparatus obtaining absorption information (X-ray transmittance image) and phase information (X-ray differential phase contrast image and X-ray phase shift image) about the X-rayed object according to the embodiments of the present invention has the following configuration.

The X-ray apparatus includes an X-ray generator generating an X-ray and a splitting element spatially splitting the X-ray generated by the X-ray generator. The detecting unit is configured to be able to divide the X-ray into X-rays with two or more widths and emit the X-rays onto the detecting unit.

Thus, the splitting element is configured to allow the detecting unit to detect the X-rays each having a different correlation between an X-ray positional change quantity and an X-ray intensity change quantity between the X-rays with two or more widths, based on which the absorption information and the phase information can be obtained independently as follows.

More specifically, the X-ray apparatus includes the detecting unit detecting an X-ray intensity by converting a positional change quantity of the X-ray based on a phase shift of the X-ray split by the splitting element and transmitted through the object to an X-ray intensity change quantity. Further, the X-ray apparatus includes a calculating unit calculating an X-ray transmittance image which is object absorption information; and an X-ray differential phase contrast image or an X-ray phase shift image which is phase information, from the X-ray intensity obtained from the detecting unit. Furthermore, the calculating unit is configured to be able to perform calculation on the basis that the correlation between the X-ray positional change quantity and the X-ray intensity change quantity of the X-rays detected by the detecting unit is different between the X-rays with two or more widths.

The detecting unit detects the X-ray intensity specifically using an X-ray optical element converting an X-ray incident position change quantity on the detector to an X-ray intensity change quantity based on the X-ray refraction effect by the object.

Here, the X-ray optical element converting the X-ray incident position change quantity on the detector to the X-ray intensity change quantity includes the following elements.

For example, the X-ray optical element includes an element whose X-ray absorbing quantity (transmitting quantity) gradually changes according to the X-ray incident position, and an element in which the light emission quantity of an X-ray-sensitive scintillator gradually changes according to the X-ray incident position.

Alternatively, the X-ray optical element includes an element whose X-ray shielding area gradually changes according to the X-ray incident position, and an element in which the absorbing quantity (transmitting quantity) of the light emitted by an X-ray-sensitive scintillator gradually changes according to the X-ray incident position.

Still alternatively, the X-ray optical element includes an element in which the shielding area of the light emitted by a scintillator gradually changes according to the X-ray incident position or an element in which the transmittance of the light emitted by a scintillator gradually changes according to the X-ray incident position.

The element whose X-ray absorbing quantity (transmitting quantity) gradually changes according to the X-ray incident position and an element in which the light emission quantity of the light emitted by a scintillator gradually changes can be implemented by changing the shape of the absorbing body or the scintillator in a gradual or stepwise manner.

Alternatively, the element can also be implemented by changing the X-ray absorbing quantity (transmitting quantity) per unit volume in a gradual or stepwise manner.

Note that the term "gradual" in the description may include the concept of "stepwise".

Further, the element whose X-ray shielding area gradually changes according to the X-ray incident position and the element in which the shielding area of the light emitted by the scintillator gradually changes can be implemented by using a light shielding element such as a mask for the X-ray or the light emitted by the scintillator.

Furthermore, the element in which the absorbing quantity (transmitting quantity) of the light emitted by the scintillator gradually or stepwise changes can be implemented by using a light reducing element formed on a substrate by gradually changing the thickness of a metal film.

The X-ray splitting element spatially splitting an X-ray incident on the X-ray optical element is used such that the X-ray split by the X-ray splitting element has two or more widths on the detector.

For example, the X-ray splitting element has a slit array structure in which slits with two types of widths are alternately arranged.

The use of such an element allows the correlation between the X-ray positional change quantity and the X-ray intensity change quantity to be different between the X-rays with two or more widths, based on which the absorption information and the phase information can be independently obtained. A specific description will follow.

First Embodiment

Referring to FIG. 1, the first embodiment will focus on an X-ray apparatus capable of independently obtaining the absorption information and the phase information using an element whose X-ray absorbing quantity (transmitting quantity) gradually changes according to the X-ray incident position, as the X-ray optical element.

As illustrated in FIG. 1, the X-ray apparatus of the present embodiment includes a splitting element 103, an object 104, an X-ray optical element 105, and a detecting unit 106 along an optical path of an X-ray emitted by an X-ray source 101 as an X-ray generation source.

Note that moving units 109, 110, and 111 using a stepping motor to move the splitting element 103, the object 104, and the X-ray optical element 105 may be provided separately.

The object 104 can be moved as needed and thus a specific portion of the object 104 can be imaged.

The X-ray emitted by the X-ray source 101 is spatially split by the splitting element 103. More specifically, the splitting element 103 functions as a sample mask having a plurality of apertures described in PTL 2, and thus the X-ray transmitted through the splitting element 103 becomes an X-ray beam.

The splitting element 103 may have a slit array shape having a line and space or may have two-dimensionally arranged holes.

Figure 2:
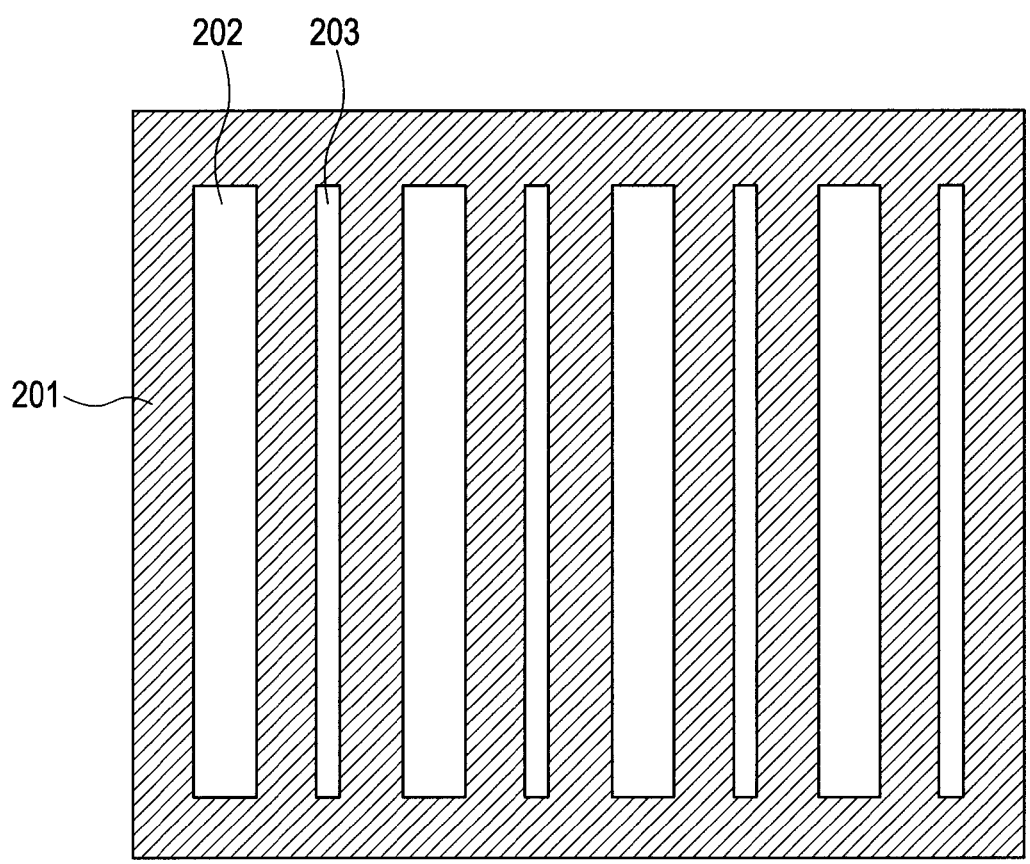
FIG. 2 is a drawing illustrating a configuration example of a splitting element according to the first embodiment.

A schematic drawing of the splitting element 103 is illustrated in FIG. 2.

The splitting element may be made of an array of slits having two or more widths periodically arranged in a line and space pattern.

Specifically, the splitting element 103 may include a substrate 201 and two types of slits 202 and 203 having different widths and being alternately arranged.

The slits 202 and 203 provided in the substrate 201 may not be penetrated through the substrate made of an optical element as long as X-rays are transmitted through.

The material of the substrate 201 is selected from Pt, Au, Pb, Ta, W, and others having high X-ray absorbing capability.

The period of the line and space arranged at the position of the detecting unit 106 detecting the X-ray split by the splitting element 103 is equal to or greater than the pixel size of the detecting unit 106.

In other word, the size of the pixels forming the detecting unit is equal to or less than the spatial period of the X-ray at the position of the detecting unit 106.

The sheet-like X-ray spatially split by the splitting element 103 is absorbed by the object 104 and its phase is changed, resulting in refraction.

Each refracted X-ray is incident on the X-ray optical element 105. The intensity of each X-ray transmitted through the X-ray optical element 105 is detected by the detecting unit 106.

The information about the X-ray obtained by the detecting unit 106 is numerically processed by the calculating unit 107 and output to a display unit 108 such as a monitor.

Examples of the object 104 include a human body and, as materials other than the human body, an inorganic material and an inorganic-organic composite material.

The detecting unit 106 is selected, for example, from an X-ray flat panel detector, an X-ray CCD camera, a direct conversion X-ray two-dimensional detector, and the like.

The detecting unit 106 may be close to the X-ray optical element 105, or may be spaced at a specific distance from each other. Alternatively, the X-ray optical element 105 may be built in the detecting unit 106.

Note that when a monochromatic X-ray is used, a monochromating unit 102 such as a monochromator combined with the slits or an X-ray multi-layer mirror may be arranged between the X-ray source 101 and the splitting element 103. In order to reduce image obscuration caused by scattered X-rays from the object 104, a grid used for X-ray radiography may be interposed between the X-ray optical element 105 and the detector 106 or between the object 104 and the X-ray optical element 105.

Figure 3:
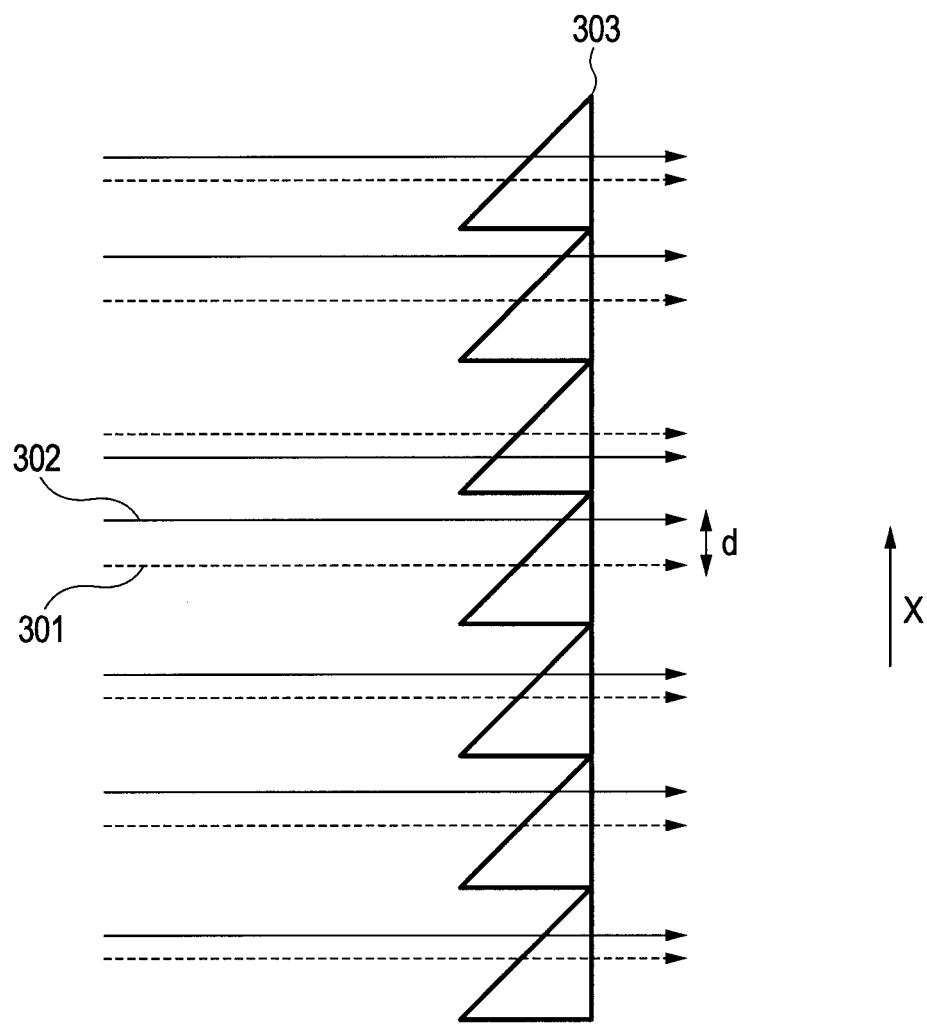
FIG. 3 is a drawing illustrating a configuration example of an X-ray optical element according to the first embodiment.

FIG. 3 is a schematic drawing of an X-ray optical element 303 describing part of the X-ray optical element 105 in FIG. 1.

A reference X-ray 301 indicates an X-ray split in the absence of the object 104. An X-ray 302 indicates an X-ray refracted by the presence of the object 104. The moving quantity d indicates the amount of the reference X-ray 301 and the X-ray 302 moving on the X-ray optical element 303 in the X direction (direction perpendicular to the X-ray incident direction).

The refraction angle of the X-ray due to a substance is very small and d is only a moving quantity at μm scale.

The X-ray optical element 303 has a triangular prism shaped array structure in which the thickness changes in the X direction.

This structure changes the optical path length of the X-ray transmitted in the X direction inside the X-ray optical element 303. In other word, the X-ray optical element 303 has an absorption gradient such that the X-ray absorbing quantity (transmitting quantity) changes depending on the X-ray incident position.

Note that the X-ray optical element 303 may be implemented by processing a plate-like member.

Figure 4:
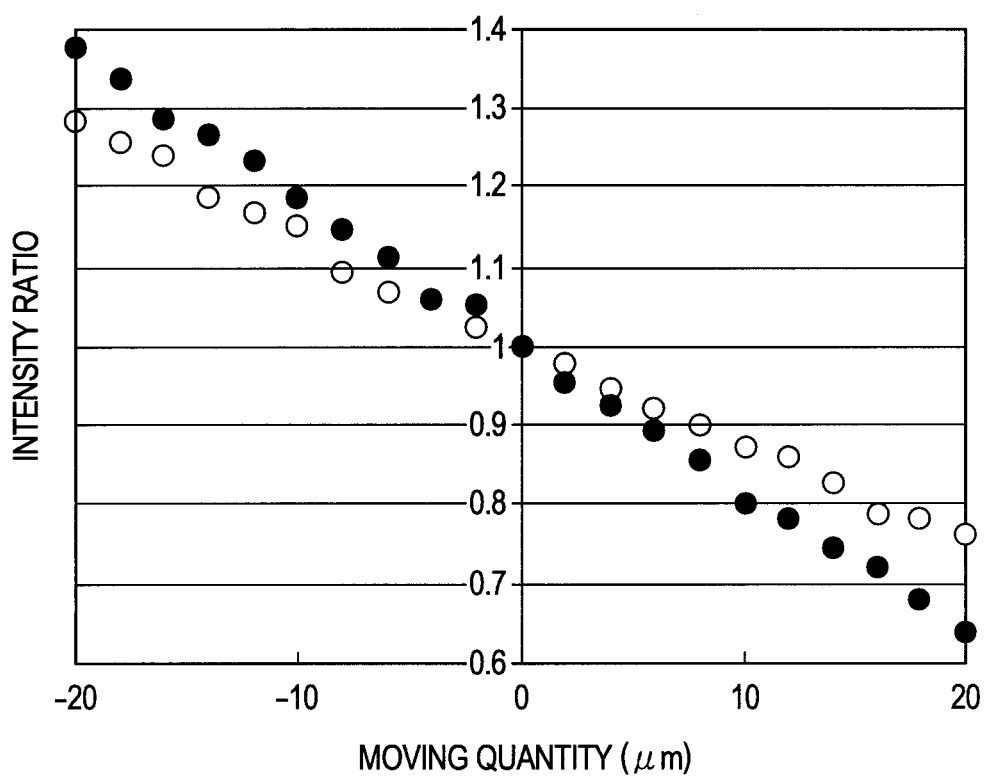
FIG. 4 is a graph illustrating a relation between an X-ray intensity ratio and a moving quantity after X-rays with different widths are transmitted through the X-ray optical element to be described in the first embodiment.

FIG. 4 is a graph illustrating a relation between an X-ray intensity ratio and a moving quantity after the splitting element 103 divides an X-ray into X-rays with different widths and the split X-rays are transmitted through the X-ray optical element.

FIG. 4 plots the moving quantity from the reference position and the intensity ratio between the reference X-ray 301 and the X-ray 302 after the splitting element 103 divides an X-ray into X-rays with two different types of widths and the X-ray optical element 303 is irradiated with the split X-rays in the absence of the object 104.

As understood from FIG. 4, both have a linear relation in a region with an extremely minute X-ray moving quantity.

The relation between the moving quantity d of the X-rays with two types of widths and intensities I1 and I2 of the reference X-ray 301 and intensities I1' and I2' of the X-ray 302 can be expressed by the following mathematical expression (1).

$$\frac{I1'}{I1} = a_1 d + b_1$$
$$\frac{I2'}{I2} = a_2 d + b_2$$

MATHEMATICAL EXPRESSION (1)

Here, $a_1$, $a_2$, $b_1$, and $b_2$ are a constant, which can be obtained by fitting the data in FIG. 4. When the object 104 is measured, considering X-ray transmittance A, the following mathematical expression (2) can be derived.

$$\frac{I1'}{AI1} = a_1 d + b_1 \quad \text{MATHEMATICAL EXPRESSION (2)}$$

$$\frac{I2'}{AI2} = a_2 d + b_2$$

With the assumption that the X-rays transmitting through the adjacent X-ray optical elements 105 are in substantially the same positions as the object 104, the two equations in the mathematical expression (2) can be solved to obtain the X-ray moving quantity d and the X-ray transmittance A to the object 104.

In this case, the information about the X-ray intensities in two adjacent elements, namely, two regions of the X-ray optical element 105 is used to obtain the transmittance A and the X-ray position moving quantity d, and thus the spatial resolution is one-half (½).

In light of this, in order to overcome the reduction in spatial resolution, in addition to the above measurement, another measurement can be made by moving the object 104 or the splitting element 103 in the X direction by the length measurable using an X-ray with another width with respect to the already measured position of the object 104.

Thereby, the information can be obtained without reducing the spatial resolution.

The use of the splitting element 103 allows the X-ray absorption information and the phase information to be obtained as independent information.

Further, the use of the X-ray optical element 105 enables detection of an X-ray position change quantity equal to or less than the pixel size of the detecting unit 106, thereby shortening the distance between the object and the detector and achieving miniaturization of the apparatus.

Figure 5:
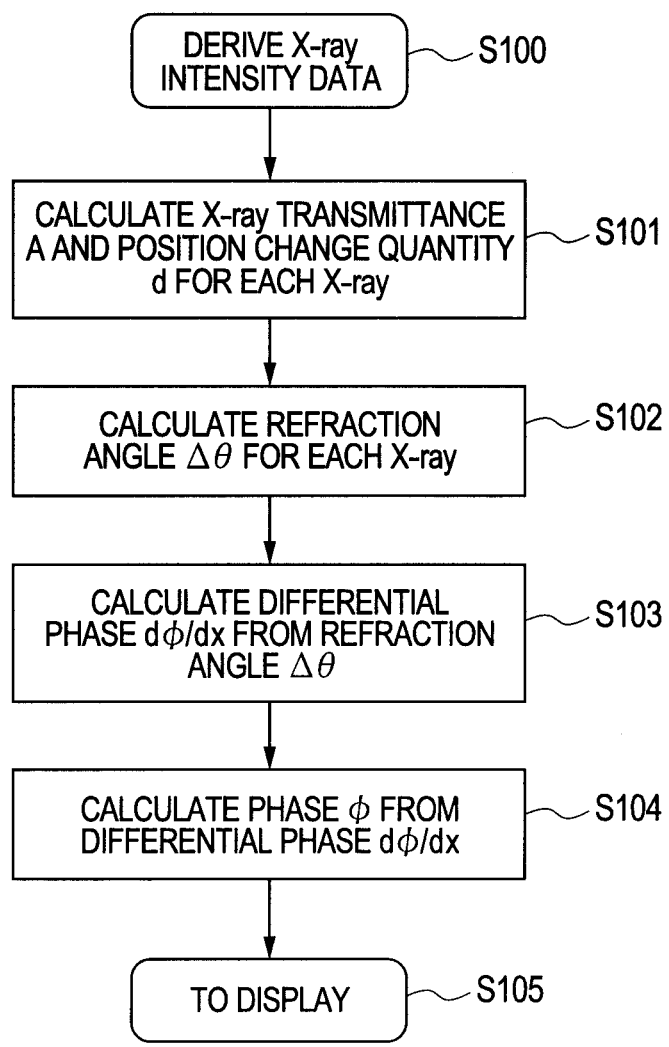
FIG. 5 is a flowchart illustrating a process flow of a calculating unit to be described in the first embodiment.

The flowchart of the calculating unit 107 is illustrated in FIG. 5. First, intensity information about each X-ray transmitted through the X-ray optical element 105 is obtained (S100).

Then, the intensity information about each X-ray is used to calculate the X-ray transmittance A and the position change quantity d with respect to the reference X-ray 301 (S101).

Using the position change quantity d and the distance Z between the object 104 and the X-ray optical element 105, each X-ray refraction angle (Δθ) can be expressed by the following mathematical expression (3).

$$\Delta\theta = \tan^{-1}\left(\frac{d}{Z}\right) \quad \text{MATHEMATICAL EXPRESSION (3)}$$

The mathematical expression (3) is used to calculate each X-ray refraction angle (Δθ) (S102).

The refraction angle (Δθ) and the differential phase (dΦ/dx) have a relation of the following mathematical expression (4).

$$\frac{d\phi}{dx} = \frac{2\pi}{\lambda}\Delta\theta \quad \text{MATHEMATICAL EXPRESSION (4)}$$

Here, λ denotes an X-ray wavelength and when a continuous X-ray is used, λ denotes an effective wavelength. The mathematical expression (4) is used to calculate each X-ray differential phase (dΦ/dx) (S103).

Then, the phase (Φ) is calculated by integrating each of the obtained differential phases (dΦ/dx) in the X direction (S104).

Thus calculated differential phase (dΦ/dx) and phase (Φ) can be displayed on the display unit 108 (S105).

This configuration enables detection of a fine X-ray positional change in one pixel of the detecting unit 106, thus eliminating the need to keep a long distance between the object 104 and the detecting unit 106 and achieving the miniaturization of the apparatus. Thus, the X-ray transmittance image, the X-ray differential phase contrast image or the X-ray phase shift image of the object can be separately obtained.

Note that a selection of a configuration keeping a long distance between the object 104 and the detecting unit 106 enables measurement of an X-ray position change based on a smaller refraction.

According to the above configuration, the X-ray refraction effect is used to detect a phase shift. Thus, a high coherence X-ray is not always required and the absorption image, the X-ray differential phase contrast image or the X-ray phase shift image can be obtained.

Note that in the above configuration, the X-ray differential phase contrast image or the X-ray phase shift image is obtained, but instead, the transmittance image obtained from the absorption information, the X-ray positional change quantity, and the refraction angle may be displayed on the display unit 108.

Second Embodiment

In the second embodiment, the description will focus on an X-ray apparatus using a phosphor array including a plurality of phosphors having a light emission quantity gradient as an X-ray optical element instead of the X-ray optical element of the first embodiment. The present embodiment describes a structure in which the X-ray optical element 105 is in contact with the detecting unit 106, but the X-ray optical element 105 may be separated from the detecting unit 106.

Here, the phosphor having a light emission quantity gradient refers to a phosphor whose light emission quantity changes depending on the X-ray incident position.

The phosphor can be implemented by gradually changing shape or gradually changing the light emission quantity per unit volume.

Note that the term "gradually" in the description may include the concept of "stepwise". For example, a stepwise changing light emission quantity is also included in the present invention.

The apparatus configuration is the same as that of the first embodiment. More specifically, the splitting element 103 periodically divides an X-ray into X-rays with two widths and the object 104 is irradiated with the X-rays. The transmitted X-rays are incident on the X-ray optical element 105. The schematic drawing of part of the X-ray optical element 105 is illustrated in FIG. 6.

A reference X-ray 601 indicates the X-ray split in the absence of the object 104. An X-ray 602 indicates the X-ray refracted by the presence of the object 104. A phosphor array 603 has a light emission quantity gradient.

Figure 6:
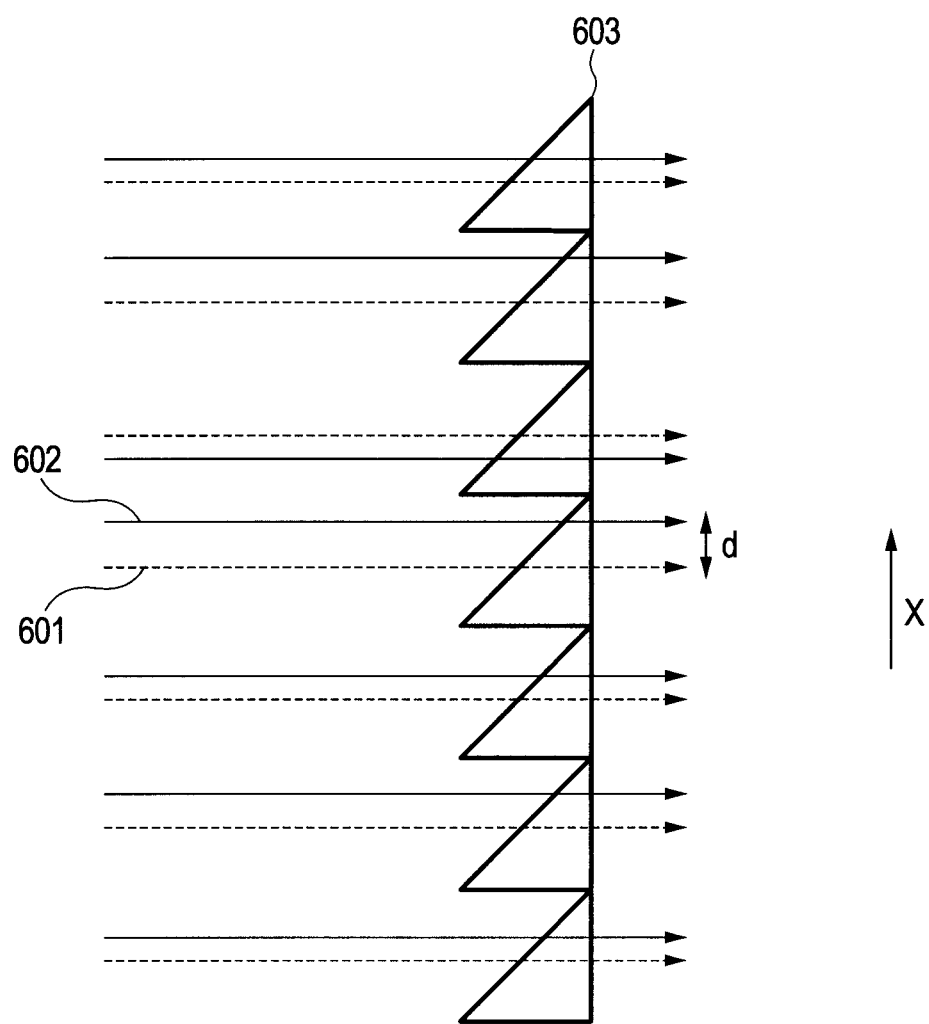
FIG. 6 is a drawing illustrating a configuration example of the X-ray optical element to be described in the second embodiment.

The phosphor array 603 is made of a material emitting phosphor light by X-ray irradiation and has gradually different shapes in the X direction in the element as illustrated in FIG. 6. As a result, the phosphor array 603 exhibits a phosphor light emission quantity distribution.

The material of the phosphor array 603 can be selected, for example, from the following generally used as an X-ray scintillator.

Specifically, the material of the phosphor array 603 can be selected from NaI (Tl-doped), CsI (Tl-doped) CsI (Nadoped), CsI (undoped), LSO (Ce-doped), YAP (Ce-doped), GSO (Ce-doped), and the like.

A visible light CCD and a COMS sensor can be used as the detecting unit 106. When X-rays with different widths are incident on the X-ray optical element 105, like the first embodiment, the light emission quantity change ratio of the phosphor array 603 with respect to the X-ray moving quantity from the reference X-ray 601 incident position is different depending on the widths.

In the absence of the object 104, the light emission quantity data is preliminarily obtained while moving the splitting element 103, thereby subjecting the moving quantity and the light emission quantity change ratio to function fitting.

Then, the same calculating unit 107 as that in the first embodiment is used to calculate the X-ray transmittance A and the position change quantity d with respect to the reference X-ray 601 from the emission information about each X-ray to calculate the differential phase quantity.

The phase can be calculated by integrating the differential phase quantity in the X direction.

In this case, the information about the X-ray intensities in two adjacent elements, namely, two regions of the X-ray optical element 105 is used to obtain the transmittance A and the X-ray position moving quantity d, and thus the spatial resolution is one-half (½).

In light of this, in order to overcome the reduction in spatial resolution, in addition to the above measurement, another measurement can be made by moving the object 104 or the splitting element 103 in the X direction by the length measurable using an X-ray with another width with respect to the already measured position of the object 104.

Thereby, the information can be obtained without reducing the spatial resolution.

This configuration enables detection of a fine X-ray positional change in one pixel of the detecting unit 106, thus eliminating the need to keep a long distance between the object 104 and the detecting unit 106 and achieving the miniaturization of the apparatus.

Thus, the X-ray transmittance image, the X-ray differential phase contrast image or the X-ray phase shift image of the object can be separately obtained.

Note that a selection of a configuration keeping a long distance between the object 104 and the detecting unit 106 enables measurement of an X-ray position change based on a smaller refraction.

According to the above configuration, the X-ray refraction effect is used to detect a phase shift. Thus, a high coherence X-ray is not always required and the absorption image, the X-ray differential phase contrast image or the X-ray phase shift image can be obtained.

Note that in the above configuration, the X-ray differential phase contrast image or the X-ray phase shift image is obtained, but instead, the transmittance image obtained from the absorption information, the X-ray positional change quantity, and the refraction angle may be displayed on the display unit 108.

Third Embodiment

In the third embodiment, the description will focus on an X-ray apparatus using a shield array including a plurality of shields for shielding part of the X-ray as an X-ray optical element instead of the X-ray optical element 105 of the first embodiment.

The present embodiment describes a structure in which the X-ray optical element 105 is in contact with the detecting unit 106, but the X-ray optical element 105 may be separated from the detecting unit 106.

Figure 7:
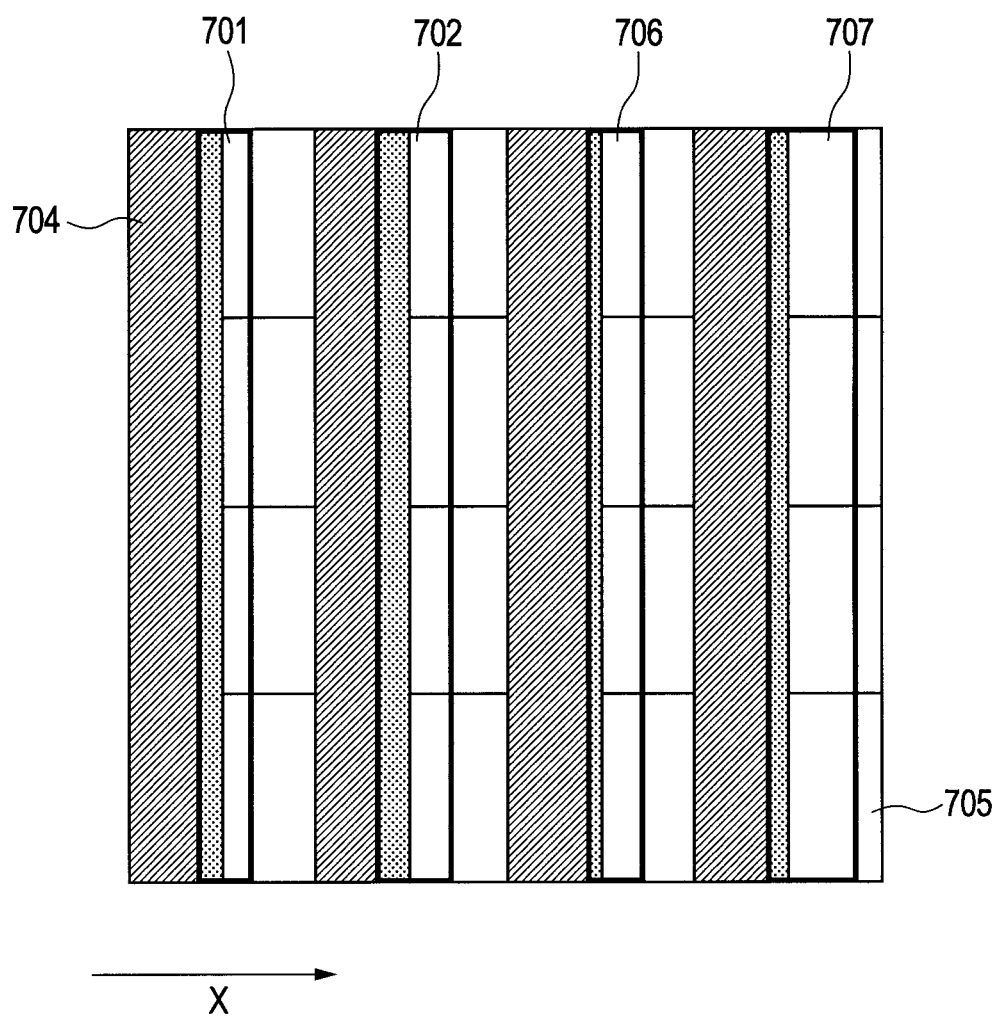
FIG. 7 is a drawing illustrating a configuration example of the X-ray optical element to be described in the third embodiment.

The schematic drawing of part of the X-ray optical element 105 is illustrated in FIG. 7.

Reference X-rays 701 and 702 with two widths indicate X-rays split in a portion without the object 104 and incident so as to pass through a center portion of a pixel 705. X-rays 706 and 707 indicate X-rays refracted by the object 104 and incident on a position shifted from the center portion of the pixel 705.

A shield 704 shields part of the reference X-rays 701 and 702 and the X-rays 706 and 707.

When the X-rays 706 and 707 move in the X direction with respect to the center portion which is the incident position of the reference X-rays 701 and 702, the shielding area of the X-rays 706 and 707 changes gradually from the shape of the shield 704. Consequently, the moving quantity can be obtained from the intensity change.

Like the first embodiment, the intensity change ratio with respect to the X-ray moving quantity with two widths exhibits a linear change with two gradients. Consequently, the same calculating unit 107 as that in the first embodiment is used.

Thus, the X-ray transmittance A and the position change quantity d with respect to the reference X-rays 701 and 702 are calculated from the intensity information about each X-ray to calculate the differential phase.

The phase can be calculated by integrating the differential phase quantity in the X direction. In this case, the information about the X-ray intensities in two adjacent elements, namely, two regions of the X-ray optical element 105 is used to obtain the transmittance A and the X-ray position moving quantity d, and thus the spatial resolution is one-half (½).

In light of this, in order to overcome the reduction in spatial resolution, in addition to the above measurement, another measurement can be made by moving the object 104 or the splitting element 103 in the X direction by the length measurable using an X-ray with another width with respect to the already measured position of the object 104.

Thereby, the information can be obtained without reducing the spatial resolution.

This configuration enables detection of a fine X-ray positional change in one pixel of the detecting unit 106, thus eliminating the need to keep a long distance between the object 104 and the detecting unit 106 and achieving the miniaturization of the apparatus.

Thus, the X-ray transmittance image, the X-ray differential phase contrast image or the X-ray phase shift image of the object can be separately obtained.

Note that a selection of a configuration keeping a long distance between the object 104 and the detecting unit 106 enables measurement of an X-ray position change based on a smaller refraction.

According to the above configuration, the X-ray refraction effect is used to detect a phase change. Thus, a high coherence X-ray is not always required and the absorption image, the X-ray differential phase contrast image or the X-ray phase shift image can be obtained.

Note that in the above configuration, the X-ray differential phase contrast image or the X-ray phase shift image is obtained, but instead, the transmittance image obtained from the absorption information, the X-ray positional change quantity, and the refraction angle may be displayed on the display unit 108.

Fourth Embodiment

In the fourth embodiment, the description will focus on an optical element for shielding part of visible light in order to convert an X-ray movement to an intensity change of the detected visible light after the X-ray is changed to the visible light by a phosphor instead of the X-ray optical element 105 of the first embodiment.

Further, the description will focus on an X-ray apparatus using the optical element such that the visible light transmittance changes gradually with a position change.

The present embodiment describes a structure in which the X-ray optical element 105 is in contact with the detecting unit 106, but the X-ray optical element 105 may be separated from the detecting unit 106.

First, referring to FIG. 8, the X-ray optical element for reducing light will be described. Specifically, the X-ray optical element 105 and the detecting unit 106 in the present embodiment will be described.

The X-ray optical element 105 and the detecting unit 106 in FIG. 1 include a scintillator 806, an optical element 803, and an optical detector 805 in the present example. The optical detectors 805 are arranged two dimensionally and thus each optical detector 805 corresponds to a pixel of a detected image. The scintillator 806 may be sensitive to X-rays and is made of cesium iodide (CsI) and the like.

The optical detector 805 may be sensitive in a light-emitting wavelength region of the scintillator and is made of a CCD, a CMOS, or the like.

Figure 8:
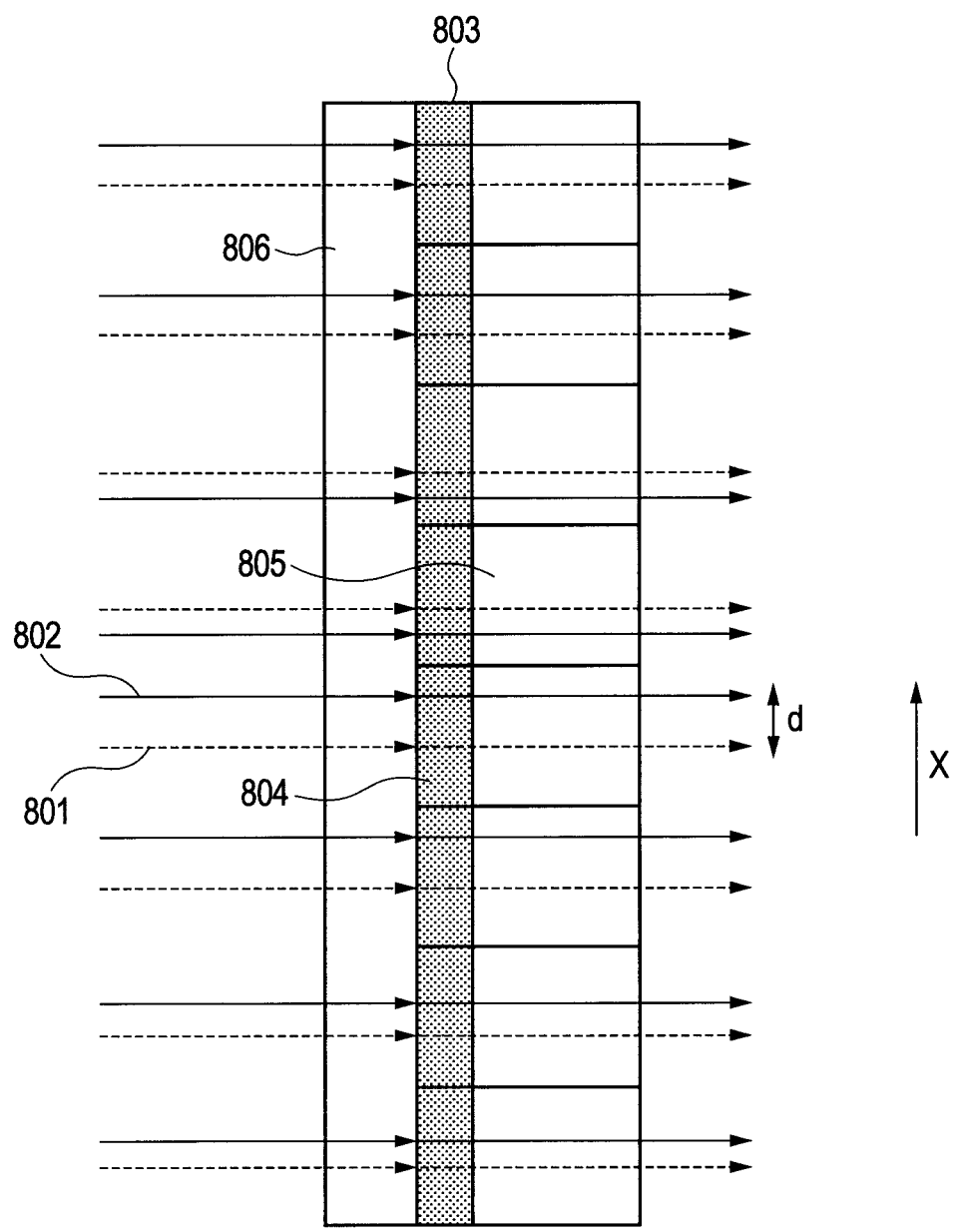
FIG. 8 is a drawing illustrating a configuration example of the X-ray optical element to be described in the fourth embodiment.

Note that the scintillator 806, the optical element 803, and the optical detector 805 may be integrally formed as illustrated in FIG. 8, but may be spaced from each other.

In FIG. 8, a reference X-ray 801 indicates an X-ray split in the absence of the object 104, and an X-ray 802 indicates an X-ray refracted by the presence of the object 104.

The reference X-ray 801 can be set to pass through a center portion of the pixel of the optical detector 805.

The optical element 803 includes a plurality of optical filters 804. The optical filter 804 is a filter such that a light transmittance changes gradually in the X direction (direction perpendicular to an incident X-ray).

The optical filter 804 is formed, such as by laminating metal on a light transmitting substrate by gradually changing the film thickness. Note that the term "gradually" in the description may include the concept of "stepwise".

According to such a configuration, when the X-ray 802 moves in the X direction with respect to the reference X-ray 801, the intensity detected by the optical detector 805 changes.

Consequently, the detected intensity can be used to obtain the position change quantity d of the object 104 from the reference X-ray 801.

Figure 9:
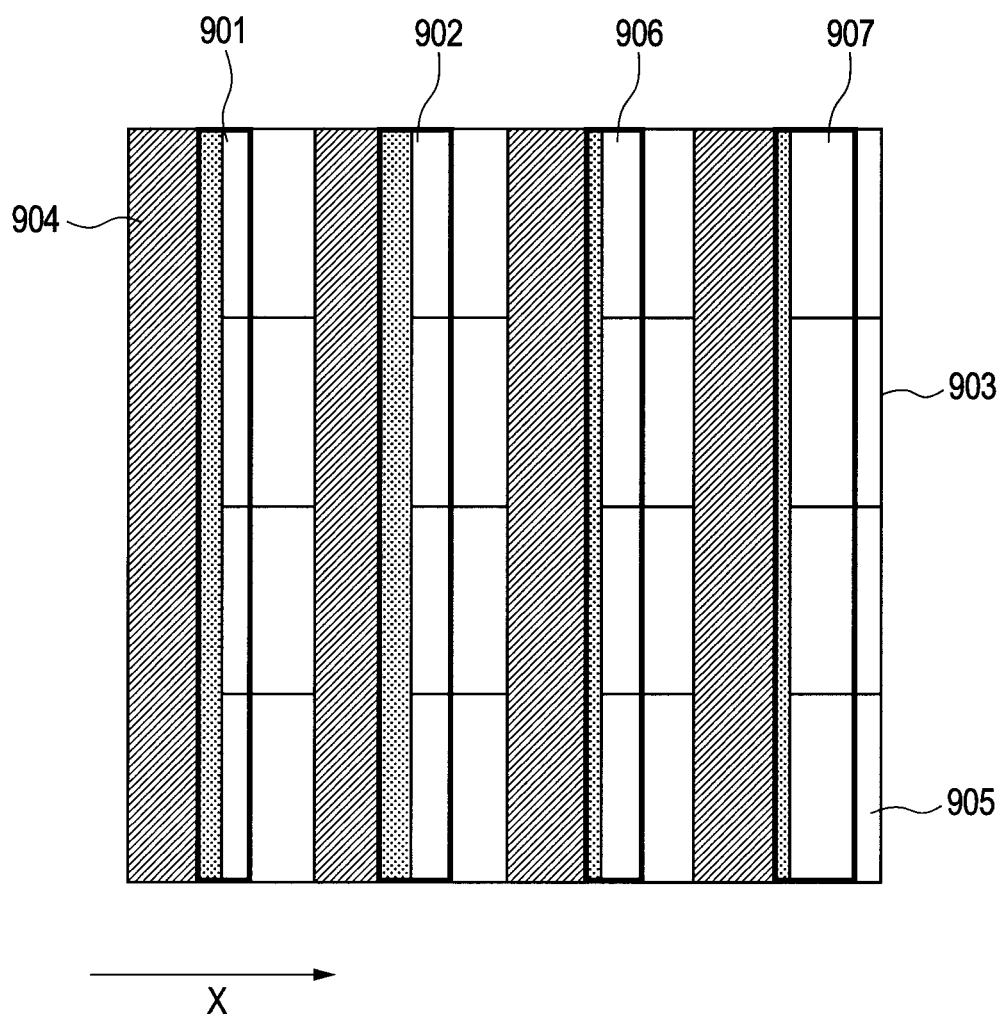
FIG. 9 is a drawing illustrating a configuration example of the X-ray optical element to be described in the fourth embodiment.

Likewise, a light shield used as the X-ray optical element is illustrated in FIG. 9.

FIG. 9 is a view of the X-ray optical element 105 and the detecting unit 106 as viewed from the X-ray incident direction.

First, the X-ray is converted to visible light by a scintillator 903 mounted on a light shield 904.

The scintillator 903 may be sensitive to X-rays and is made of cesium iodide (CsI) and the like.

The reference X-rays with two widths are converted to visible light by the scintillator, and the reference light beams 901 and 902 are incident so as to pass through a center portion of a pixel 905.

Light beams 906 and 907 indicate light beams converted to visible light after the X-rays are refracted by the object 104 and incident on a scintillator portion located in a position shifted from the center portion of the pixel 905.

The light shield 904 shields part of the reference light beams 901 and 902, and light beams 906 and 907.

When light beams 906 and 907 move in the X direction with respect to the center portion which is the incident position of the reference light beams 901 and 902, the light shielding area of the light beams 906 and 907 changes gradually from the shape of the light shield 904. Consequently, the moving quantity can be obtained from the intensity change.

The X-ray optical element 105 implementing a light reducing method and a light shielding method detects X-rays with two widths split by the splitting element 103. The detected intensity change ratio with respect to the moving quantity exhibits a linear change with two different gradients.

Thus, the same calculating unit 107 as that in the first embodiment is used. Specifically, the X-ray transmittance A and the position change quantity d are calculated from the intensity information about each X-ray to calculate the differential phase. The phase can be calculated by integrating the differential phase in the X direction.

In this case, the information about the X-ray intensities in two adjacent elements, namely, two regions of the X-ray optical element 105 is used to obtain the transmittance A and the X-ray position moving quantity d, and thus the spatial resolution is one-half (½).

In light of this, in order to overcome the reduction in spatial resolution, in addition to the above measurement, another measurement can be made by moving the object 104 or the splitting element 103 in the X direction by the length measurable using an X-ray with another width with respect to the already measured position of the object 104.

Thereby, the information can be obtained without reducing the spatial resolution.

This configuration enables detection of a fine X-ray positional change in one pixel of the detecting unit 106, thus eliminating the need to keep a long distance between the object 104 and the detecting unit 106 and achieving the miniaturization of the apparatus. Thus, the X-ray transmittance image, the X-ray differential phase contrast image or the X-ray phase shift image of the object can be separately obtained.

Note that a selection of a configuration keeping a long distance between the object 104 and the detecting unit 106 enables measurement of an X-ray position change based on a smaller refraction.

According to the above configuration, the X-ray refraction effect is used to detect a phase change. Thus, a high coherence X-ray is not always required and the absorption image, the X-ray differential phase contrast image or the X-ray phase shift image can be obtained.

Note that in the above configuration, the X-ray differential phase contrast image or the X-ray phase shift image is obtained, but instead, the transmittance image obtained from the absorption information, the X-ray positional change quantity, and the refraction angle may be displayed on the display unit 108.

EXAMPLE

Figure 10:
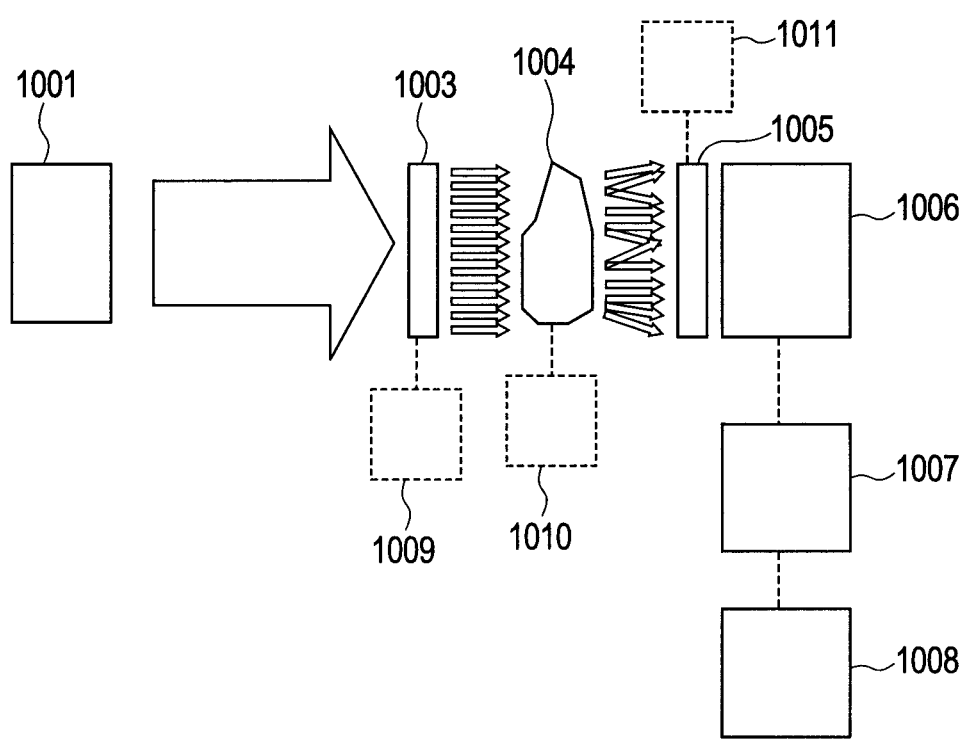
FIG. 10 is a drawing illustrating a configuration of an apparatus to be described in an example.

Referring to FIG. 10, the X-ray apparatus and the X-ray measuring method according to an example of the present invention will be described.

As the X-ray generator, a rotating-anticathode-type X-ray generator having an Mo target illustrated in an X-ray source 1001 is used.

The X-ray is spatially split by the splitting element 1003 arranged in a position spaced 100 cm from the X-ray source. The splitting element 1003 is formed by alternately arranging tungsten (w) with a thickness of 100 µm and slit widths of 50 µm and 30 µm. The slit period is 100 µm.

Note that as the material, not only w but also Au, Pb, Ta, and Pt can be used.

The X-rays split by the splitting element 1003 are emitted to the object 1004. The X-rays transmitted through the object 1004 are incident on the X-ray optical element 1005. Note that moving units 1009, 1010, and 1011 each using a stepping motor are provided in the splitting element 1003, the object 1004, and the X-ray optical element 1005.

The X-ray optical element 1005 is formed by arranging Ni triangular prisms on a carbon substrate with a thickness of 1 mm, a bottom length of 150 µm and a height of 75 µm.

The X-ray detector 1006 is arranged such that the X-rays transmitted through the X-ray optical element 1005 are projected on the X-ray detector 1006 at a period of 200 µm and the X-ray intensity is detected.

Subsequently, the splitting element 1005 is moved 100 µm in a periodic direction of the triangular prisms using the moving unit 1009 to perform similar measurement.

The X-ray detector 1006 is a flat panel detector with a pixel size of 50 µm×50 µm. The X-ray intensity values of four pixels in a periodic direction of the triangular prisms are totaled to produce the X-ray intensity of one X-ray optical element.

In the absence of the object 1004, the X-ray intensity data is preliminarily acquired while moving the splitting element 1003 in one direction. Thereby, data about the relation between the position change quantity and the X-ray intensity change ratio regarding the X-rays split by the splitting element 1003 and the X-ray optical element of each X-ray is obtained.

The data subjected to function fitting is used by the calculating unit 1007 to calculate the X-ray transmittance (A) and the position change quantity (d) of each X-rayed object 1004. Then, the refraction angle ($\Delta\theta$) is calculated by the mathematical expression (3).

The differential phase is calculated from the refraction angle ($\Delta\theta$) by the mathematical expression (4). The differential phases obtained from each X-ray are spatially integrated to obtain the X-ray phase shift image. In the calculation of the differential phase, 0.71 Å which is an Mo characteristic X-ray is used as the wavelength.

The X-ray transmittance image, the X-ray differential phase contrast image, and the X-ray phase shift image obtained by the calculating unit 1007 are displayed on a PC monitor as the display unit 1008.

This application claims the benefit of Japanese Patent Application No. 2010-177062, filed Aug. 6, 2010, which is hereby incorporated by reference herein in its entirety.

The invention claimed is:

1. An X-ray apparatus for deriving X-ray absorbing information and X-ray phase information of an object to be detected comprising:
   a splitting element for splitting spatially X-rays generated by an X-ray generator into X-ray beams;
   a detector unit for detecting intensities of the X-rays, based on the X-rays split by said splitting element and transmitted through the object, the intensity of the X-rays changing according to an X-ray phase shift during the transmitting of the X-rays through the object, and also changing according to an X-ray position change; and
   a calculating unit for calculating an X-ray transmittance image as the X-ray absorbing information, and an X-ray differential phase contrast image or an X-ray phase shift contrast image as the X-ray phase information by using the intensities of the X-rays, wherein
   said splitting element forms X-ray beams by splitting the X-rays, and the X-ray beams have two or more widths at said detector unit,
   said calculating unit calculates the X-ray absorbing information and the X-ray phase information, based on a changing, in correlation between the changing of the phase of the X-rays and the changing the intensity of the X-rays in said detector unit, the correlation being changed according to the width of X-ray beam,
   wherein said splitting element comprises a slit array formed by line and space such that a slit width changes periodically between two or more slit widths, and
   wherein said slit array formed by line and space is formed by arranging alternatingly two slits of different widths.

2. The X-ray apparatus according to claim 1, further comprising an X-ray optical element arranged between said splitting element and said detector unit, and formed from an element for converting the position change quantity generated by the phase shift through the object into the intensity change of the X-rays.

3. The X-ray apparatus according to claim 2, wherein said element forming the X-ray optical element comprises a plurality of members absorbing or transmitting the X-rays arranged perpendicularly to an X-ray incident direction, and said member is formed into a triangular prism shape to have absorbing capability gradient so that an X-ray absorbing quantity or an X-ray transmitting quantity changes according to an X-ray incident position.

4. The X-ray apparatus according to claim 2, wherein said element forming the X-ray optical element comprises a plurality of shields shielding a part of the X-rays arranged perpendicularly to an X-ray incident direction, so that an area shielded by said shield changes according to an X-ray incident position.

5. The X-ray apparatus according to claim 1, further comprising an optical element arranged between said splitting element and said detector unit,
   wherein an element forming said optical element comprises a plurality of phosphors sensing the X-rays arranged perpendicularly to an X-ray incident direction, to have a light emitting quantity gradient so that the light emitting quantity of the phosphor changes according to an X-ray incident position.

6. The X-ray apparatus according to claim 1, further comprising an optical element arranged between said splitting element and said detector unit,
   wherein an element forming the optical element comprises a plurality of optical filters arranged perpendicularly to an X-ray incident direction, so that a light transmittance of said filters changes according to an X-ray incident position.

7. The X-ray apparatus according to claim 2, wherein said calculating unit calculates the X-ray transmittance image and the X-ray phase shift image of the object, under an assumption that the X-rays being transmitted to said elements forming said X-ray optical element and being adjacent to each other contain information of the same position of the object.

8. The X-ray apparatus according to claim 1, further comprising
   an optical element comprising a plurality of elements arranged between said splitting element and said detector unit, wherein
   said calculating unit calculates the X-ray transmittance image and the X-ray position change of the object, under an assumption that the X-rays being transmitted to elements forming the X-ray optical element and being adjacent to each other contain information of the same position of the object.

9. An X-ray apparatus for deriving X-ray absorbing information and X-ray phase information of an object to be detected comprising:

a splitting element for splitting spatially X-rays generated by an X-ray generator into X-ray beams;

a detector unit for detecting intensities of the X-rays, based on the X-rays split by said splitting element and transmitted through the object, the intensity of the X-rays changing according to an X-ray phase shift during the transmitting of the X-rays through the object, and also changing according to an X-ray position change;

a calculating unit for calculating an X-ray transmittance image as the X-ray absorbing information, and an X-ray differential phase contrast image or an X-ray phase shift contrast image as the X-ray phase information by using the intensities of the X-rays; and an X-ray optical element arranged between said splitting element and said detector unit, and formed from an element for converting the position change quantity generated by the phase shift through the object into the intensity change of the X-rays, wherein said splitting element forms X-ray beams by splitting the X-rays, and the X-ray beams have two or more widths at said detector unit, said calculating unit calculates the X-ray absorbing information and the X-ray phase information, based on a changing, in correlation between the changing of the phase of the X-rays and the changing the intensity of the X-rays in said detector unit, the correlation being changed according to the width of X-ray beam, and a plurality of the elements each forming the X-ray optical element include a first element and a second element, and said calculating unit calculates the X-ray transmittance image and the X-ray position change of the object according to following mathematical expressions:

$$\frac{I1'}{AI1} = a_1 d + b_1$$

$$\frac{I2'}{AI2} = a_2 d + b_2$$

where

I1 is an intensity of X-rays being transmitted through the first element when the object is not arranged between the X-ray generator and the detector unit, I2 is an intensity of X-rays being transmitted through the second element when the object is not arranged between the X-ray generator and the detector unit, I1' is an intensity of X-rays being transmitted through the first element when the object is arranged between the X-ray generator and the detector unit, I2' is an intensity of X-rays being transmitted through the second element when the object is arranged between the X-ray generator and the detector unit, A is X-ray transmittance, d is X-ray position moving quantity, a1 and b1 are constants determined based on a relation between the X-ray intensity ratio and the X-ray position moving quantity of the width of the X-ray incident in the first element, and a2 and b2 are constants determined based on a relation between the X-ray intensity ratio and the X-ray position moving quantity of the width of the X-ray incident in the second element.

10. An X-ray apparatus for deriving X-ray absorbing information and X-ray phase information of an object to be detected comprising:

a splitting element for splitting spatially X-rays generated by an X-ray generator into X-ray beams;

a detector unit for detecting intensities of the X-rays, based on the X-rays split by said splitting element and transmitted through the object, the intensity of the X-rays changing according to an X-ray phase shift during the transmitting of the X-rays through the object, and also changing according to an X-ray position change;

a calculating unit for calculating an X-ray transmittance image as the X-ray absorbing information, and an X-ray differential phase contrast image or an X-ray phase shift contrast image as the X-ray phase information by using the intensities of the X-rays; and an optical element arranged between said splitting element and said detector unit, and including a first element and a second element, and wherein said calculating unit calculates the X-ray transmittance image and the X-ray position change of the object according to following mathematical expressions:

$$\frac{I1'}{AI1} = a_1 d + b_1$$

$$\frac{I2'}{AI2} = a_2 d + b_2$$

where

I1 is an intensity of the X-rays being transmitted through the first element when the object is not arranged between the X-ray generator and the detector unit, I2 is an intensity of the X-rays being transmitted through the second element when the object is not arranged between the X-ray generator and the detector unit, I1' is an intensity of the X-rays being transmitted through the first element when the object is arranged between the X-ray generator and the detector unit, I2' is an intensity of the X-rays being transmitted through the second element when the object is arranged between the X-ray generator and the detector unit, A is X-ray transmittance, d is X-ray position moving quantity, a1 and b1 are constants determined based on a relation between the X-ray intensity ratio and the X-ray position moving quantity of the width of the X-ray beam incident on the first element, and a2 and b2 are constants determined based on a relation between the X-ray intensity ratio and the X-ray position moving quantity of the width of the X-ray beam incident in the second element, wherein said splitting element forms X-ray beams by splitting the X-rays, and the X-ray beams have two or more widths at said detector unit, and said calculating unit calculates the X-ray absorbing information and the X-ray phase information, based on a changing, in correlation between the changing of the phase of the X-rays and the changing the intensity of the X-rays in said detector unit, the correlation being changed according to the width of X-ray beam.

11. The X-ray apparatus according to claim 10, wherein said splitting element comprises a slit array formed by line and space such that a slit width changes periodically between two or more slit widths.

12. The X-ray apparatus according to claim 11, wherein said slit array formed by line and space is formed by arranging alternatingly two slits of different widths.

* * * * *